(12) United States Patent
Leysieffer

(10) Patent No.: US 6,198,971 B1
(45) Date of Patent: Mar. 6, 2001

(54) IMPLANTABLE SYSTEM FOR REHABILITATION OF A HEARING DISORDER

(75) Inventor: Hans Leysieffer, Taufkirchen (DE)

(73) Assignee: IMPLEX Aktiengesellschaft Hearing Technology, Ismaning (DE)

( * ) Notice: Subject to any disclaimer, the term of this patent is extended or adjusted under 35 U.S.C. 154(b) by 0 days.

(21) Appl. No.: 09/369,182

(22) Filed: Aug. 6, 1999

(30) Foreign Application Priority Data

Apr. 8, 1999 (DE) .............................. 199 15 846

(51) Int. Cl.[7] ...................................... A61N 1/00
(52) U.S. Cl. ................................. 607/55; 607/59
(58) Field of Search ................. 607/55–57, 59, 607/60; 600/25

(56) References Cited

U.S. PATENT DOCUMENTS

| 3,557,775 | 1/1971 | Mahoney . |
| 3,712,962 | 1/1973 | Epley . |

(List continued on next page.)

FOREIGN PATENT DOCUMENTS

| 0 190 836 | 8/1986 | (EP) . |
| 0 200 321 | 11/1986 | (EP) . |
| 0 263 254 | 4/1988 | (EP) . |
| 0 499 939 | 8/1992 | (EP) . |
| 0 823 188 | 10/1996 | (WO) . |
| WO 97/18689 | 5/1997 | (WO) . |
| WO 98/03035 | 1/1998 | (WO) . |
| WO 98/06237 | 2/1998 | (WO) . |
| WO 98/26629 | 6/1998 | (WO) . |
| WO 98/36711 | 8/1998 | (WO) . |
| wo 99/07436 | 2/1999 | (WO) . |
| wo 99/08475 | 2/1999 | (WO) . |
| wo 99/08481 | 2/1999 | (WO) . |

OTHER PUBLICATIONS

Yanagihara et al., Implantable Hearing Aid, Arch Otolaryngol Head Neck Surg., vol. 113, Aug. 1987 pp. 869–872.
Suzuki, Middle Ear Implant: Implantable Hearing Aids, Karger, vol. 4, pp. 160–169.
H. Leysieffer et al., Ein Vollständig Implantierbares Hörsystem Für Innenohrschwerhörige: TICA LZ 3001, HNO, 1998; 46 Pages 853–863, Springer–Verlag 1998.
Zenner et al., Erste Implantationen Eines Vollständig Implantierbaren Elektronischen Hörsystems Bei Patienten Mit Innenohr–Schwerhörigkeit, HNO 1998; 46 Pages 844–852, Springer–Verlag 1998.
Hörakustik, Tinnitus–Retraining–Therapie Und Hörakustik, Die Küftigen Aufgaben Der Hörgeräte–Akustiker, Quartal 1997, ISSN 0945–0556–1H7545–Einzelpreis: 15 DM, Feb. 1997, pp. 26 and 27.
H. Leysieffer et al., Einvollständig Implantierbares Hörsystem Für Innenohrschwerhörige: TICA LZ 3001, HNO 1998; 46, pp. 853–863.

*Primary Examiner*—Jeffrey R. Jastrzab
(74) *Attorney, Agent, or Firm*—Nixon Peabody LLP; David S. Safran

(57) ABSTRACT

An at least partially implantable system for rehabilitation of a hearing disorder with an arrangement for processing and/or generation of signals is provided including an implantable processor arrangement with control logic which operates according to an operating program and an implantable storage arrangement for storage of the operating program and of operating parameters. A wireless telemetry unit is provided for data transmission between the implantable part of the system and an external unit. The system also includes a power supply arrangement which supplies individual components of the system with current and a rewritable implantable storage arrangement assigned to the processor arrangement for holding and reproducing the operating program and the operating parameters. At least a part of the operating program and/or of the operating parameters can be modified and/or replaced by data transmitted from the external unit via the telemetry unit.

28 Claims, 6 Drawing Sheets

U.S. PATENT DOCUMENTS

| | | |
|---|---|---|
| 3,764,748 | 10/1973 | Branch et al. . |
| 4,352,960 | 10/1982 | Dormer et al. . |
| 4,441,210 | 4/1984 | Hochmair et al. . |
| 4,729,366 | 3/1988 | Schaefer . |
| 4,850,962 | 7/1989 | Schaefer . |
| 4,998,333 | 3/1991 | Skyttä . |
| 5,015,224 | 5/1991 | Maniglia . |
| 5,015,225 | 5/1991 | Hough et al. . |
| 5,070,535 | 12/1991 | Hochmair et al. . |
| 5,095,904 | 3/1992 | Seligman et al. . |
| 5,271,397 | 12/1993 | Seligman et al. . |
| 5,277,694 | 1/1994 | Leysieffer et al. . |
| 5,411,467 | 5/1995 | Hortmann et al. . |
| 5,597,380 | 1/1997 | McDermott et al. . |
| 5,601,617 | 2/1997 | Loeb et al. . |
| 5,603,726 | 2/1997 | Schulman et al. . |
| 5,624,376 | 4/1997 | Ball et al. . |
| 5,626,629 | 5/1997 | Faltys et al. . |
| 5,795,287 | 8/1998 | Ball et al. . |
| 5,814,095 | 9/1998 | Müller et al. . |
| 5,859,916 | 1/1999 | Ball et al. .- |

IMPLANTABLE SYSTEM FOR REHABILITATION OF A HEARING DISORDER

BACKGROUND OF THE INVENTION

1. Technical Field

This invention relates to an at least partially implantable system for rehabilitation of a hearing disorder with an arrangement for processing and/or generating signals, which includes an implantable processor arrangement with control logic which operates according to an operating program and an implantable memory arrangement for storage of the operating program and of operating parameters. Also, the invention relates to systems including a wireless telemetry means for data transmission between the implantable part of the system and an external unit, and a power supply arrangement which supplies individual components of the system with current.

2. Description of Related Art

Rehabilitation of sensory hearing disorders with partially implantable electronic systems in recent years has acquired major importance. The expression "hearing disorder" is defined here as inner ear damage, middle ear damage, combined inner ear and middle ear damage, cochlear deafness which necessitates use of a cochlea implant, likewise retrocochlear hearing disorders which necessitate use of an auditory brain stem implant, i.e. briefly, everything which prevents or adversely affects sound reception and/or relay to the brain stem. "Hearing disorders" here furthermore include temporary or permanent noise in the ears (tinnitus). In particular, the use of partially implantable electronic systems applies to the group of patients in which hearing has completely failed due to accident, illness or other effects or is congenitally absent. If, in these cases, only the inner ear (cochlea), and not the neuronal auditory path which leads to the center, is affected, the remaining auditory nerve can be stimulated with electrical stimulation signals and thus a hearing impression can be produced which can lead to clear understanding of speech. In these so-called cochlea implants, an array of stimulation electrodes, which is triggered by an electronic system, is inserted into the cochlea. This hermetically tight and biocompatibly encapsulated electronic module is surgically embedded in the bony area behind the ear (mastoid). However, the electronic system contains essentially only decoder and driver circuits for the stimulating electrodes, sound reception and conversion of this acoustic signal into electrical signals, while their further processing takes place basically externally in a so-called speech processor which is carried outside on the body. The speech processor converts the preprocessing signals coded accordingly into a high frequency carrier signal which via inductive coupling is transmitted through the closed skin (transcutaneously) to the implant. The sound-receiving microphone is located without exception outside the body, and in most applications, in a housing of a behind-the-ear hearing aid worn on the external ear, and is connected to the speech processor by a cable. These cochlea implant systems, their components and principles of transcutaneous signal transmission are described by way of example in U.S. Pat. No. 5,070,535, U.S. Pat. No. 4,441,210, published European patent application No. 0 200 321 and U.S. Pat. No. 5,626,629. Methods of speech processing and coding in cochlea implants are disclosed for example, in published European patent No. 0 823 188, published European patent No. 0 190 836, U.S. Pat. No. 5,597,380, U.S. Pat. No. 5,271,397, U.S. Pat. No. 5,095,904, U.S. Pat. No. 5,601,617 and U.S. Pat. No. 5,603,726.

In addition to the rehabilitation of deaf patients, or those who have lost their hearing, using cochlea implants, for some time there have been approaches to offer better rehabilitation using partially or fully implantable hearing aids than with conventional hearing aids to patients with sensorineural hearing disorder which cannot be surgically corrected. The principle consists, in most embodiments, in directly stimulating an ossicle of the middle ear or the inner ear via mechanical or hydromechanical stimulation and not via the amplified acoustic signal of a conventional hearing aid in which the amplified acoustic signal is sent to the external auditory canal. The actuator stimulus of these electromechanical systems is accomplished with different physical transducer principles such as, for example, by electromagnetic and piezoelectric systems. The advantage of these processes lies mainly in the sound quality which is improved compared to conventional hearing aids and, for fully implanted systems, in the fact that the hearing prosthesis is not visible. These partially and fully implantable electromechanical hearing aids are described, for example, by Yanigahara et al. in Arch Otolaryngol Head Neck, Surg-Vol 113, August 1987, pp. 869–872; Suzuki et al. in Advances in Audiology, Vol. 4, Karger Basel, 1988; Leysieffer et al. in HNO, Vol. 46, 1998, pp. 853–863; Zenner et al. in HNO, Vol. 46, 1998, pp. 844–852; and in numerous patent documents, especially in commonly assigned U.S. patent application Ser. No. 09/097,710, in U.S. Pat. Nos. 4,850,962; 5,277,694; 5,411,467; 5,814,095; 3,764,748; 4,352,960; 5,015,224; 5,015,225; 3,557,775; 3,712,962; 4,729,366; 4,998,333; and 5,859,916, published European Patent No. 0 263 254, published PCT Application Nos. 98/36711; 98/06237; 98/03035; 99/08481; 99/08475; 99/07436; and 97/18689.

Many patients with inner ear damage also suffer from temporary or permanent noise in the ears (tinnitus) which cannot be surgically corrected and against which there are no drug forms of treatment to date. Therefore, so-called tinnitus maskers are available; they are small, battery-driven devices which are worn like a hearing aid behind or in the ear. By means of artificial sounds which are emitted via, for example, a hearing aid speaker into the auditory canal, the maskers mask the tinnitus by psychoacoustic means and thus reduce the disturbing noise in the ears, as much as possible, below the threshold of perception. The artificial sounds are often narrowband noise (for example, third-octave noise) which can be adjusted in its spectral location and loudness level via a programming device to enable adaptation to the individual tinnitus situation as optimally as possible. In addition, recently, the so-called retraining method has been introduced in which by combination of a mental training program and presenting broadband sound (noise) near the resting hearing threshold, the perceptibility of the tinnitus is likewise to be largely suppressed Journal "Hoerakustik" 2/97, pages 26 and 27). The devices used in this training program are also called "noisers".

In the two aforementioned methods for hardware treatment of tinnitus, hearing aid-like technical devices must be worn visibly outside on the body in the area of the ear. These devices stigmatize the wearer and therefore are not willingly worn.

U.S. Pat. No. 5,795,287 discloses an implantable tinnitus masker with direct drive of the middle ear, for example, via an electromechanical converter, coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

Implantable systems for the treatment of tinnitus by masking and/or noiser functions have been proposed, in which corresponding electronic modules are added to the signal-processing electronic path of a partially or fully implantable hearing system such that the signals necessary for tinnitus masking or noiser functions can be fed into the signal processing path of the hearing aid function and the pertinent signal parameters can be adapted by further electronic measures individually to the pathological requirements. This adaptability can be accomplished by the necessary setting data of the signal generation and feed electronics being filed or programmed in the same physical and logic data storage area of the implant system. Also, the feed of the masker or noiser signal into the audio path of the hearing implant can be controlled via the corresponding electronic means.

In all the above-described rehabilitation devices, it now seems to be a good idea to design the systems such that they can be completely implanted. These hearing systems, depending on the desired function, consist of three or four function units: a sensor (microphone) which converts the incident airborne sound into an electrical signal; an electronic signal processing, amplification and implant control unit; an electromechanical or implantable electroacoustic transducer which converts the amplified and preprocessed sensor signals into mechanical or acoustic vibrations and sends the signals, via suitable coupling mechanisms, to the damaged middle and/or inner ear, or a cochlear stimulation electrode for cochlea implants; and an electric power supply system which supplies the aforementioned modules. Furthermore, there can be an external unit which makes available electrical recharging energy to the implant when the implant-side power supply unit contains a rechargeable (secondary) battery. Especially advantageous devices and processes for charging of rechargeable implant batteries are described in commonly assigned U.S. patent application Ser. No. 09/311,566 and in published European patent No. 0 499 939. Feasibly, a telemetry unit can also be provided with which patient-specific, audiological data can be transmitted bidirectionally or programmed in the implant and thus permanently stored, as was described by Leysieffer et al. in HNO Vol. 46, 1998, pp. 853–863.

Basically, in all the above-described at least partially implantable systems, the (audio) signal processing or signal generation and the modules of the implant control are built, for example, like a controlled battery recharging system or a telemetry system for bidirectional transmission of, for example, variable, patient-specific parameters on the implant-side by permanently fixed hardware units. This design feature also applies in cases in which digital signal processors or microcontrollers or microprocessors are used for signal processing or generation or for implant management, regardless of whether they are built as so-called "hardwired logic", i.e. in "hardwired" logic architecture, or whether their operating programs are filed in the read-only memories (ROM) of the corresponding processors. These programs, which are provided and necessary for basic operation of the implant and for proper operation, are called hereinafter the operating program or operating software. This operating software is placed in the implant systems described in the prior art during production, for example, by mask programming of the processor storage areas and can no longer be changed after implantation.

In contrast, patient-specific data such as, for example, audiologic adaptation data or also variable implant system parameters (for example, as a variable in one of the aforementioned software programs for controlling battery recharging) are referred to as operating parameters. These operating parameters can be transmitted transcutaneously to the implant according to the aforementioned prior art in fully implantable implant systems after implantation, i.e. wirelessly through the closed skin and, thus, can be changed.

If, on the other hand, the operating software is to be changed because, for example, due to more recent scientific findings, improved algorithms for speech signal processing are available in, for example, fully implanted cochlea implants or electromechanical hearing systems for rehabilitation of an inner ear disorder, the entire implant or implant module which contains the corresponding signal processing unit must be replaced by a new unit containing the altered operating software by invasive surgery on the patient. This surgery entails renewed medical risks for the patient, and is especially serious in the application of cochlea implants in children as patients. In addition, the surgery is very costly. In addition, this system change can only be done completely, especially in cochlea implants, i.e. with removal of the stimulation electrode, since a technically very complex, multipin and detachable plug connection to the signal processing implant module is not used given the currently conventional large number of stimulus channels.

SUMMARY OF THE INVENTION

Accordingly, it is a primary object of this invention to provide an at least partially implantable system for rehabilitation of a hearing disorder in which signal processing and generation can be better adapted than in existing systems after implantation.

The implantable system of the present invention, on the one hand, enables matching of system functions to patient-specific circumstances which can often only be ascertained after implantation of the system and, on the other hand, enables new medical and audiologic findings in signal processing or generation of the already implanted system to be taken into account.

This object is achieved by providing an at least partially implantable system for rehabilitation of a hearing disorder of the initially mentioned type which includes a rewritable implantable storage arrangement assigned to a processor arrangement for holding and reproducing an operating program, wherein at least parts of the operating program can be modified or replaced by data transmitted from an external unit via a telemetry means. In this way, after implantation of the implantable system, not only can the operating parameters be transferred from the external unit to the implanted system, but the operating software as such can also be modified or completely replaced.

The storage arrangement for storage of operating parameters and the storage arrangement for holding and reproducing the operating program can be implemented as storage arrangements independent of one another; however it can also be a single storage arrangement in which both the operating parameters and also operating programs can be filed.

The approach of the present invention allows matching of the system to circumstances which can be acquired only after implantation of the implantable system. Thus, for example, in an at least partially implantable hearing system for rehabilitation of a monaural or binaural middle ear and/or inner ear disorder and tinnitus with electrical and/or mechanical and/or acoustic stimulation of the middle ear, inner ear or the higher neuronal structures of the auditory path, the sensor (acoustic sensor or microphone) and actuator (output stimulator) biological interfaces are always dependent on anatomic, biological and neurophysiological circumstances, for example on the individual healing process. These interface parameters can also be time-variant. Thus, for example, the response of an implanted microphone can vary individually and between individuals based on the tissue coverings, the response of an electromechanical transducer coupled to the ossicular chain or directly to the inner ear based on different coupling quality, or the response of an intracochlear electrode based on different electrode impedances and the electrode position in a cochlea implant or brain stem implant.

These differences of interface parameters, which cannot be eliminated or reduced in the devices disclosed in the prior art simply by replacing the implant, can now be optimized in the system of the present invention by changing or improving the signal processing of the implant.

In an at least partially implantable hearing system with electrical and/or mechanical and/or acoustic stimulation of the middle ear, inner ear or the higher neuronal structure of the auditory canal, it can be a good idea or even necessary to implement signal processing algorithms which have been improved after implantation. Regardless of the type of stimulation (electrical, mechanical, acoustic) the following signal processing algorithms could be used: voice analysis processes (for example, optimization of a fast Fourier transform (FFT)); static or adaptive noise detection processes; static or adaptive noise suppression processes; processes for optimization of the signal to noise ratio within the system; optimized signal processing strategies in progressive hearing disorder; output level limiting processes for protection of the patient in implant malfunctions or external faulty programming; methods of preprocessing of several sensors (microphone) signals, especially for binaural positioning of the sensors; processes for binaural processing of two or more sensor signals in binaural sensor positioning, for example optimization of spacial hearing or space orientation; phase or group delay time optimization in binaural signal processing; and processes for optimized driving of the output stimulators, especially for binaural positioning of the stimulators.

If output stimulation takes place mechanically and/or acoustically, the following signal processing algorithms can be implemented with the system of the present invention even after implantation: a process for feedback suppression or reduction; a process for optimization of the operating process of the output transducer(s) (for example frequency response and phase response optimization, and improvement of the impulse response); a voice signal compression process for inner ear hearing disorders; and signal processing methods for recruitment compensation in inner ear hearing disorders.

Furthermore, in implant systems with a secondary power supply unit, i.e. a rechargeable battery system, but also in systems with primary battery supply, it can be assumed that as technology advances, these electrical power storages will allow longer service lives and thus increasing residence times in the patients. It can be assumed that research on principles and applications for signal processing algorithms is making rapid progress. The necessity or patent desire for operating software adaptation and modification will, therefore, presumably take place before the service life of the implanted power source expires. While in known systems with hardware-linked operating software, adaptation of the operating software required surgical replacement of the implant, the system described here allows this adaptation of the operating programs of the implant even when it is already implanted.

The present invention may also include a buffer storage arrangement in which data transmitted from the external unit via the telemetry means can be buffered before being relayed to the arrangement for processing and/or generating signals. In this way, the transmission process from the external unit to the implanted system can be closed before the data transmitted via the telemetry means is relayed to the arrangement for processing and/or generating signals. Furthermore, checking logic may be provided to check the data stored in the buffer storage arrangement before being relayed to the arrangement for processing and/or generating signals.

The arrangement for processing and/or generating signals may be implemented in a microcontroller, which advantageously also contains the checking logic and the buffer storage arrangement, and an implantable storage arrangement preferably being assigned to the microcontroller. At least portions of a working program for the microcontroller may be changed or replaced by data transferred from the external unit via the telemetry means.

The buffer storage arrangement and the storage arrangement for storage of the working program for the microcontroller can be implemented as independent storages; but there can also be a single storage in which both data transferred from the external unit and working programs for the microcontroller can be filed.

In another embodiment of the invention, there may be at least two storage areas for holding and reproducing the operating program. Like the two aforementioned measures for reliability of the system, this design is also advantageous in that checking for the absence of faults in the software can be done, for example, after transmission from the exterior or when the implant is turned on due to the multiple presence of the storage area which contains the operating program(s).

Similarly, the buffer storage arrangement can also have two storage areas for holding and reproducing data transferred from the external unit via the telemetry means so that, after data transmission from the external unit in the area of the buffer, the absence of errors in the transferred data can be checked. For example, the memory areas can be designed for complementary filing of the data transferred from the external unit,. At least one of the storage areas of the buffer storage arrangement however can also be designed to hold only part of the data transferred from the external unit resulting in the absence of errors in the transferred data being checked in sections.

To ensure that a new transmission process can be started in case of transmission errors, a preprogrammed read only memory area, which cannot be overwritten, can be assigned to the processor arrangement. The instructions and parameters necessary for "minimum operation" of the system are stored in the ROM area. For example, the instructions may include instructions which, after a "system crash", ensure at least error-free operation of the telemetry means for receiving an operating program and instructions for storage thereof in the control logic.

As already mentioned, the telemetry means is advantageously designed, not only for the reception of operating programs from the external unit, but also for the transfer of operating parameters between the implantable part of the system and the external unit such that, on the one hand, these parameters can be adjusted by a physician, a hearing aid acoustics specialist or the wearer of the system himself (for example, loudness) and, on the other hand, the system can also transfer the parameters to the external unit, for example, to check the status of the system.

If the at least partially implantable system for rehabilitation of a hearing disorder is a tinnitus masker, a noiser or a hearing aid with tinnitus masker or noiser functions, the system of the present invention preferably has a digital arrangement for generation of electrical signals and an arrangement downstream of the digital arrangement for generating stimuli, in this case masker or noiser signals, based on the electrical signals generated by the digital arrangement. If the at least partially implantable system for rehabilitation of a hearing disorder is a hearing aid, according to another aspect of this invention, the invention includes at least one acoustic sensor, a digital arrangement for processing of the acoustic signals acquired by means of at least one acoustic sensor, and an arrangement for generating stimuli based on processing of the acoustic signals acquired by at least one acoustic sensor.

Depending on the function of the implant (especially cochlea implant, brain stem implant, tinnitus masker, noiser, hearing aid with or without tinnitus masker or noiser function), the arrangement for generating stimuli can comprise an array of stimulation electrodes for application of electrical cochlea or brain stem stimuli, one or more electroacoustic transducers, one or more electromechanical transducers which can also be piezoelectric transducers, or one or more electromagnetic transducers.

Conventionally the power supply arrangement of the system of the present invention advantageously comprises a rechargeable electrochemical cell which can be recharged from the outside, for example, by means of inductive coupling.

DETAILED DESCRIPTION OF THE INVENTION

Figure 1:
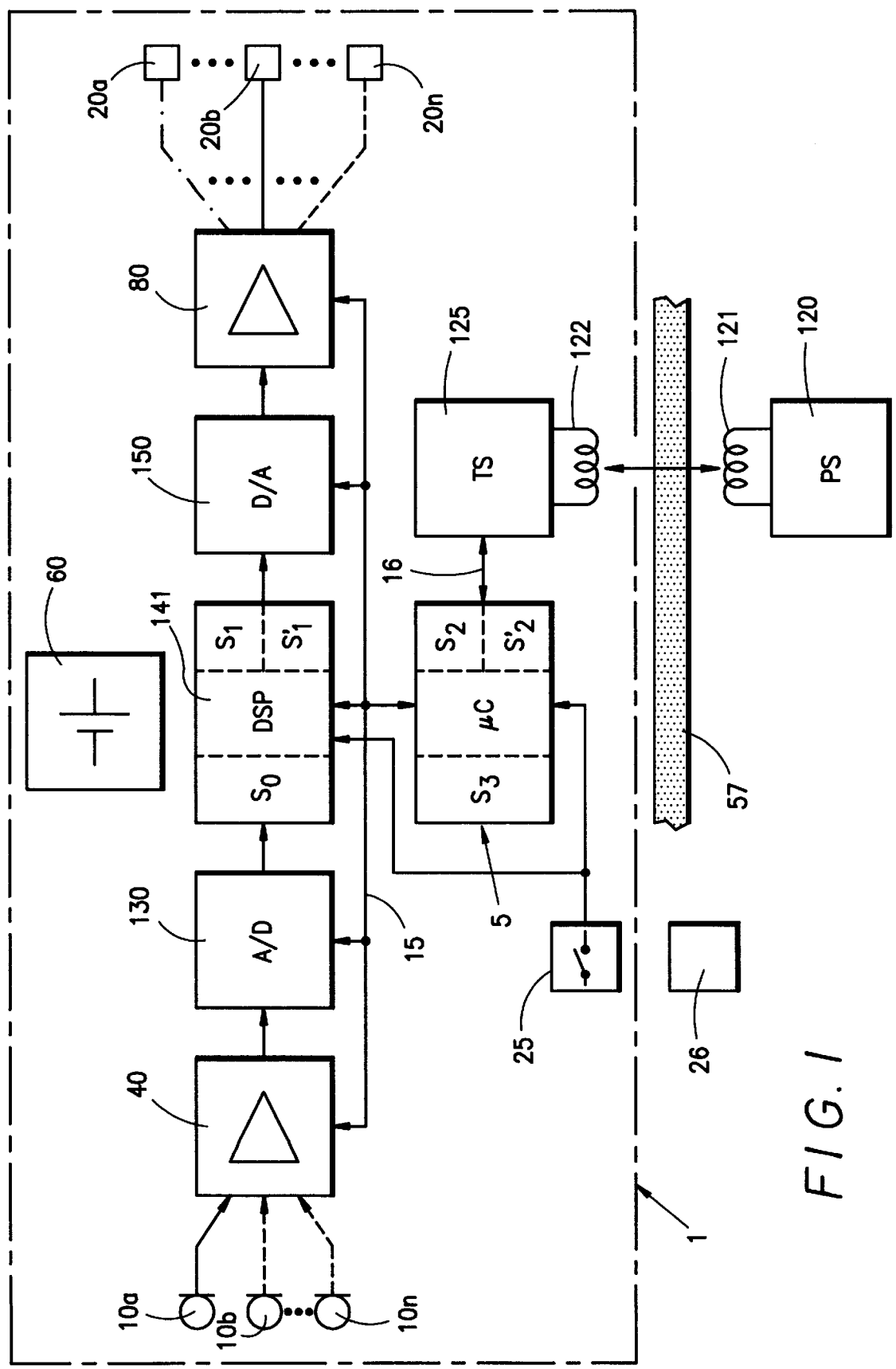
FIG. 1 is a schematic block diagram of an at least partially implantable hearing system for rehabilitation of a middle ear and/or inner ear disorder, or for treatment of tinnitus.

FIG. 1 shows a schematic block diagram of an at least partially implantable hearing system 1 for rehabilitation of a middle ear and/or inner ear disorder or tinnitus with electrical and/or mechanical and/or acoustic stimulation of the middle ear, inner ear or the higher neuronal structures of the auditory path. The external acoustic signal is received via one or more acoustic sensors (microphones) 10a to 10n and is converted into electrical signals. In the case of implantation for exclusive rehabilitation of tinnitus by masking or noiser functions without additional hearing aid function, these sensor functions are eliminated. The electrical sensor signals are routed to a module 40 in which the sensor signal or signals are selected and preprocessed. This preprocessing can consist, for example, of analog linear or nonlinear preamplification and filtering (for example anti-aliasing filtering). The preprocessed sensor signal leads to an analog-digital converter 130 (A/D). When using a plurality of sensors, there can be a corresponding plurality of A/D converters. The digitized sensor signal(s) are supplied to a digital signal processor 141 (DSP) which executes the intended function of the hearing implant, for example, audio signal processing in a system for inner ear hearing disorders and/or signal generation in the case of a tinnitus masker or noiser. The DSP 141 contains a read only memory area $S_0$ which cannot be overwritten and in which the instructions and parameters necessary for "minimum operation" of the system are stored. The DSP 141 also contains a storage area $S_1$ in which the operating software of the intended function or functions of the implant system are filed. As already mentioned, this storage area can also be present twice ($S_1$'). The rewritable program storage for holding the operating software can be based on EEPROM or RAM cells, and in this case provisions should be made for this RAM area to always be "buffered" by the power supply system within the implant.

The digital output signals of the DSP 141 are converted in a digital to analog converter 150 (D/A) into analog signals. There can be more than one D/A converter, depending on the implant function. Alternatively, the D/A connector can be completely eliminated if, for example, in the case of a hearing system with an electromagnetic output converter, a pulse-width modulated, serial digital output signal of the DSP 141 is transferred directly to the output converter. The analog output signal(s) of the digital to analog converter 150 are then routed to a driver unit 80 which depending on the implant function triggers the output stimulator 20a. There can be more than one of both the driver unit 80 and also the output stimulator 20a (20a to 20n), for example in the case of a cochlea implant or brain stem implant with several electrical stimulation electrodes as output stimulators.

In the embodiment shown in FIG. 1, the signal processing components 40, 130, 141, 150, and 80 are controlled by a microcontroller 5 (μC) with one or two associated storages ($S_2$ and $S_2$') via a bidirectional data bus 15. In the storage area(s) $S_2$ and $S_2$', the operating software portions of the implant management system can be filed (for example, administration, monitoring and telemetry functions). Memories $S_1$ and/or $S_2$ can also file patient-specific, for example audiologic adaptation, parameters which can be altered from the outside. Furthermore, the microcontroller 5 has a rewritable storage $S_3$ in which a working program for the microcontroller 5 is filed.

The microcontroller 5 communicates via a data bus 16 with a telemetry system 125 (TS). This telemetry system 125 in turn communicates wirelessly through the closed skin 57 via the inductive coil coupling shown by way of example in FIG. 1 (implant coil 122 and external coil 121) bidirectionally with an external programming system 120 (PS) which can advantageously be a computer with the corresponding programming, processing, display and administration software. Via this telemetry interface, the operating software of the implant system 1 which is to be changed or completely replaced is transmitted and buffered first of all in the storage area $S_2$ of the microcontroller 5. The storage area $S_2$' may be used for complementary filing of the data transferred from the external system, and coincidence of the contents of storage areas $S_2$ and $S_2$' may be checked before changing or replacing the content of the rewritable storage $S_3$ in conformity the content of storage areas $S_2$. The operating software of the implantable hearing system 1 is to be understood to include both the operating software of the microcontroller 5

(for example housekeeping functions such as energy management or handling of the telemetry functions) as well as the operating software of the digital signal processor 141. Thus, for example, simple verification of software transmission can be done by a reading process via the telemetry interface before the operating software, or the corresponding signal processing portions of this software, are transmitted into the program storage area $S_1$ of the digital signal processor 141 via the data bus 15. Furthermore, the working program for the microcontroller 5, stored for example in the rewritable storage $S_3$, can be changed or replaced in whole or in part via the telemetry interface 125 using the external unit 120.

All electronic components of the implant system are supplied by a primary or secondary battery 60 with electrical operating energy.

Figure 6:
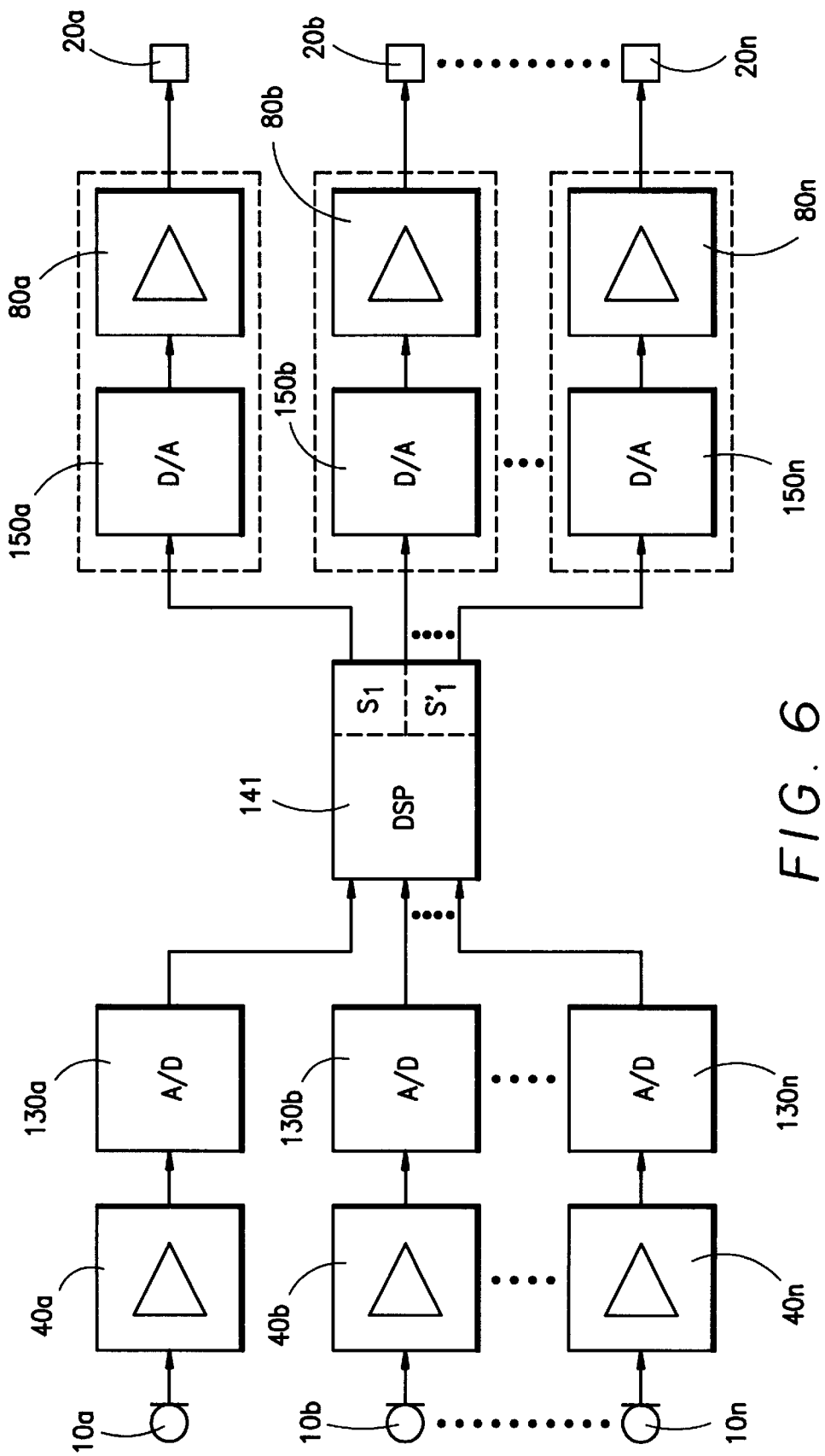
FIG. 6 is a schematic view of a modified embodiment of the arrangement for processing and/or generation of signals.

According to FIG. 6, downstream of the acoustic sensors (microphones) 10a to 10n, respective preprocessing modules 40a to 40n and respective analog-digital converters 130a to 130n are connected. In a corresponding manner, according to FIG. 6, upstream of the output stimulators 20a to 20n, respective digital-to-analog converters 150a to 150n and respective driver units 80a to 80n are connected. Depending on the intended implant function, on the output side, the digital to analog converters 150a to 150n and the driver units 80a to 80n for the output stimulators 20a to 20n can be functionally combined, as is illustrated in FIG. 6 by the broken outlines. For example, in the case of a cochlea implant with several stimulation electrodes, the digital output values delivered by the digital signal processor 141 can be sent to digitally programmable current sources which deliver the corresponding current-modulated and time-modulated electrical stimulation signals to the electrodes. In the case of a hearing system with one or more electromagnetic output converters, the digital to analog converters 150a to 150n can also be completely eliminated when the outputs of the digital signal processor 141 deliver pulse-width modulated serial data and pertinent time integration takes place by the transducer or transducers themselves.

Figure 2:
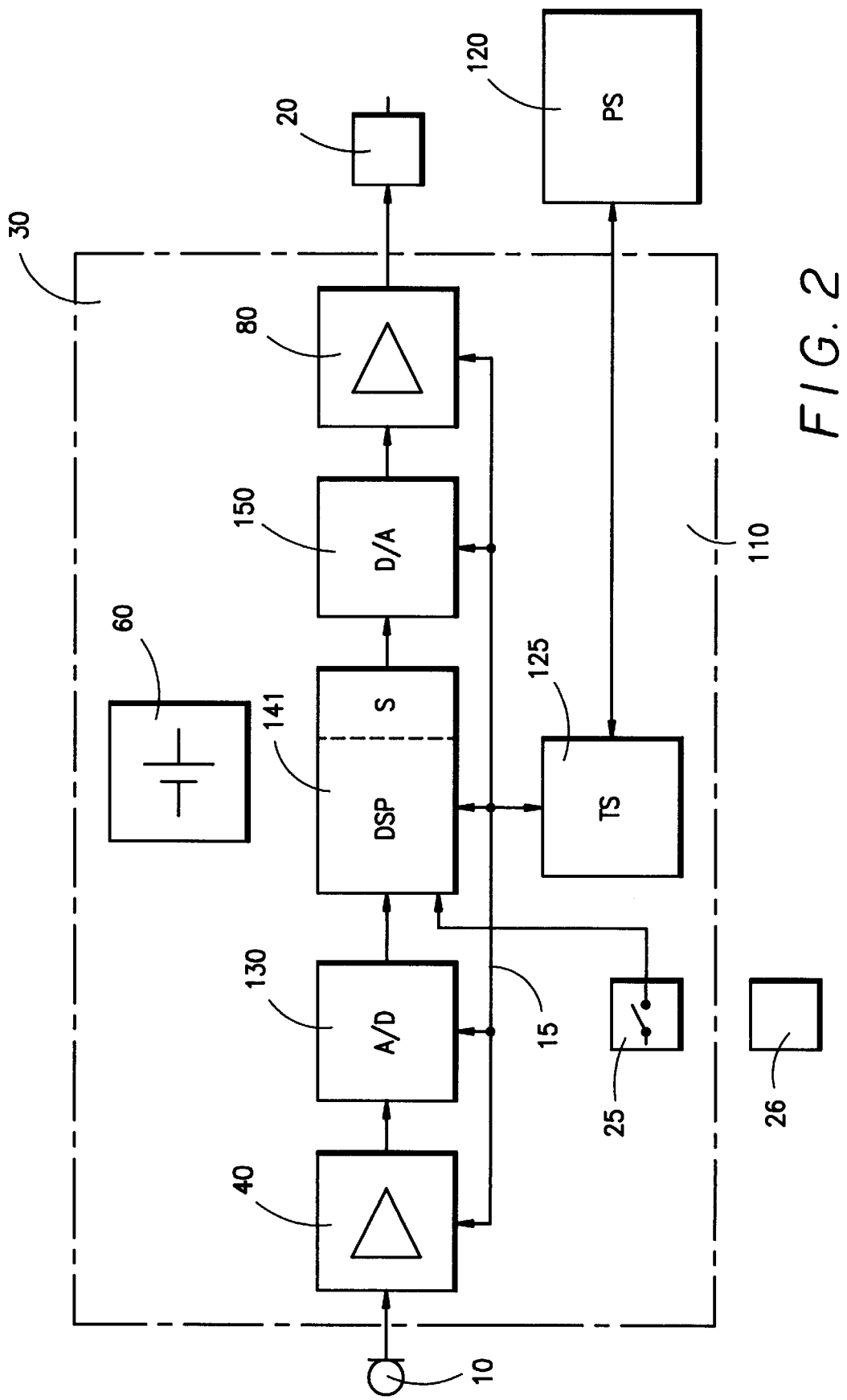
FIG. 2 is a block diagram similar to FIG. 1 of a technically simplified embodiment of the system of the present invention.

The technically simplified embodiment as shown in FIG. 2 differs from that of FIG. 1 essentially only in that in the module 30, which comprises all the implant electronics and the electrical power storage, a signal processor 141 (DSP) is provided which in addition assumes the functions of the microcontroller 5 as shown in FIG. 1. FIG. 2 shows only one sensor 10 and one output stimulator 20 as well as the overall storage area S of the DSP 141 which contains all variable operating and management software parts and also patient-specific parameters. In this case, the DSP 141 directly communicates bidirectionally via the data bus 15 with the telemetry system 125 (TS).

Figure 3:
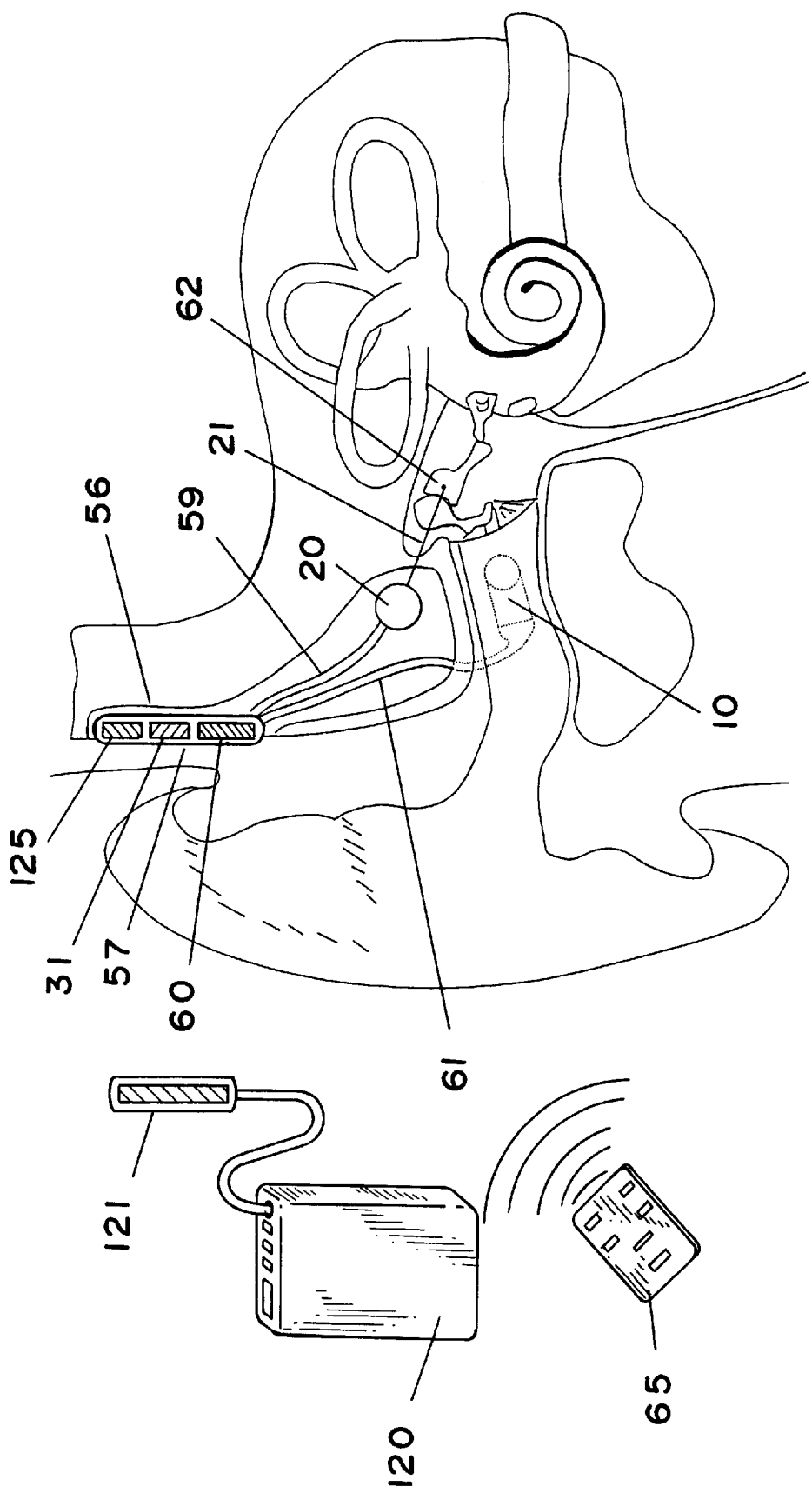
FIG. 3 is a schematic view of a hearing system of the present invention implanted in the head of a patient and the pertinent external units.

FIG. 3 schematically shows one possible embodiment of a fully implantable hearing system for individuals with inner ear disorders which includes a sensor (microphone) and an electromechanical output transducer with transcutaneously alterable operating software according to FIGS. 1, 2 and 6. In particular, a hermetically tight and biocompatible implant housing 56 holds an electronic module 31 as was described with reference to FIGS. 1, 2 and 6. Furthermore, the housing 56 contains a battery 60 for electrical supply to the implant and the telemetry means 125. A sensor 10 (microphone) which has been subcutaneously implanted in the rear wall of the auditory canal receives the sound and converts it into an electrical signal which is supplied via the implant line 61 to the electronic module in the housing 56. One especially advantageous microphone for use in the system described here is described in U.S. Pat. No. 5,814,095.

The audiologically processed and amplified signal is sent via the implantable line 59 to the electromechanical transducer 20. This transducer 20, in this example, is shown as a directly coupled system, i.e. the output-side mechanical oscillations of the transducer 20 are directly coupled via a suitable coupling element 21 to an ossicle of the middle ear chain, i.e. to the anvil 62. The transducer oscillations travel via the ossicle chain to the inner ear and cause the corresponding auditory impression. Suitable coupling elements are described, for example, in published German patent application No. 197 38 587 and the corresponding commonly assigned U.S. patent application Ser. No. 09/042,805. Advantageous transducers for use in the systems described herein are disclosed in U.S. Pat. No. 5,277,694 and in commonly assigned U.S. patent applications Ser. Nos. 09/275,872 and 09/311,563.

Furthermore, FIG. 3 shows an external programming system 120 with which the operating software to be replaced or changed can be transcutaneously transmitted. To do this, a transmitting and reading head with a coil 121 is used and placed over the implant for bidirectional data transmission by transferring the data inductively. If the battery 60 in the implant housing 56 is a secondary rechargeable element, the implantable unit can also contain power receiving circuit for implant-side preparation of recharging energy. Then the external system 120 with the transmitting coil 121 also contains a wireless charger. One advantageous embodiment of an implantable unit with a receiving coil is described in commonly assigned U.S. patent application Ser. No. 09/311, 565. FIG. 3 furthermore illustrates a portable remote control unit 65 with which the wearer of the system can change or adjust important hearing system functions.

Figure 4:
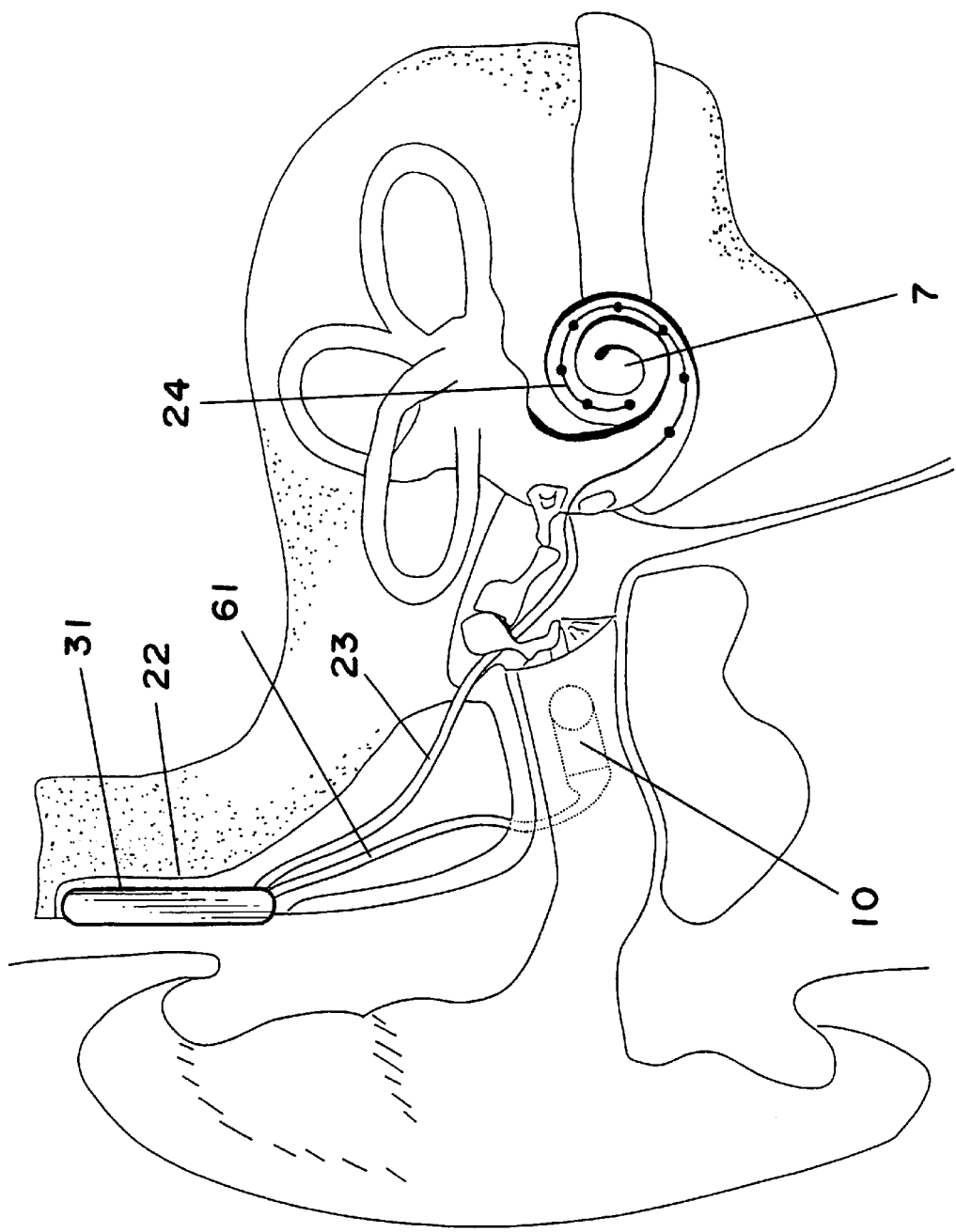
FIG. 4 is a schematic view of an implanted hearing system of the present invention designed as a cochlea implant.

FIG. 4 illustrates, by way of example, a completely implantable cochlea implant with transcutaneously variable operating software as shown in FIGS. 1, 2 and 6. An acoustic sensor 10 (microphone) receives external acoustic signals and transmits the signals as electrical sensor signals to a hermetically tight and biocompatible electronic module 31 which is fixed in an artificial bone bed 22 on the mastoid plane. The electronic module 31 contains the implant components as shown in FIGS. 1, 2 and 6. Via a multipin line 23 on the output side, a multichannel electrical stimulation electrode 24 is connected which is placed in the cochlea 7. The external modules necessary for transfer of the operating software can be made identical to that in FIG. 3 and are therefore not shown in FIG. 4.

Figure 5:
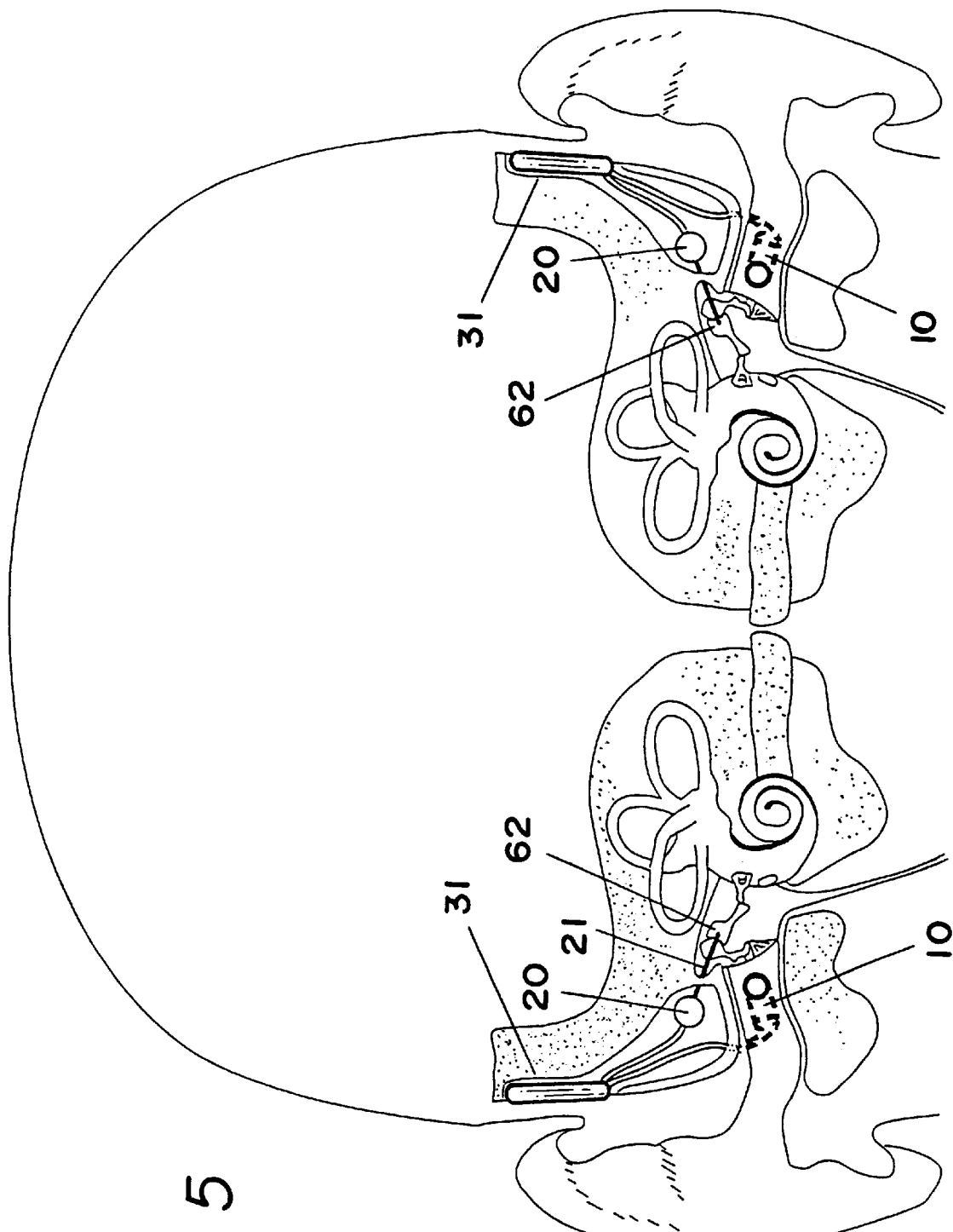
FIG. 5 is a schematic view of a binaural hearing system of the present invention implanted in the head of a patient.

The subject invention is applicable not only for monaural but also for binaural rehabilitation of any kind of the above described hearing disorders. FIG. 5 shows by way of example a completely implantable hearing system for binaural supply of a bilateral inner ear hearing loss with electromechanical stimulation of the impaired inner ears. On each side, there is an implanted acoustic sensor (microphone) 10 for example as shown in FIG. 3 and 4. The electrical sensor signals travel to the hermetically tight and biocompatibly made electronic modules 31 which are positioned likewise on each side on the mastoid plane and which process the sensor signals. The modules 31 may contain signal processing and power supply components as shown in FIG. 1, 2 and 6.

The output signals lead to electromechanical transducers 20 likewise implanted on both sides. In this example, these transducers 20 are coupled via the corresponding coupling elements 21 directly to the ossicle chain, i.e. incus 62, of the middle ear and thus transmit the mechanical oscillations to the damaged inner ears. The two electronic modules 31 may be independent of one another, in which case provisions are preferably made for optimum mutual matching by the corresponding programming of the individual modules. The two electronic modules 31 can also however be interconnected by an electrical multipole data line, or wirelessly via an inductive or radio-based route to enable binaural signal processing as explained, for example, in published PCT application No. 98/26629. To do this in the two implant modules, there are corresponding interface units which implement galvanic coupling or wireless communication.

The following combination possibilities can be foreseen:

The two electronic modules may each contain one digital signal processor according to the aforementioned description, and the operating software of the two processors can be transcutaneously changed, as described. Then the connection of the two modules provides essentially for data exchange for optimized binaural signal processing, for example, of the sensor signals.

Only one module contains the described digital signal processor. The module connection then provides, in addition to transmission of sensor data for binaural sound analysis and balancing, for transfer of the output signal to the contralateral converter, and the latter module can house the electronic transducer driver. In this case, the operating software of the entire binaural system is filed in only one module and the software also changed in the module from the outside only transcutaneously via a telemetry unit, which is present on only one side. In this case, the power supply of the entire binaural system can be housed in only one electronic module and power to the contralateral module being supplied by wire or wirelessly.

As illustrated in FIGS. 1 and 2, the implantable hearing system 1 and the module 30, respectively, may be provided with a transcutaneously operable switch, preferably a reed switch 25, which is adapted to be actuated by placing a magnet 26 on the closed skin 57. The switch 25 may be used, for example in an emergency such as a malfunction of the hearing system, to reset the housekeeping functions of the microcontroller 5 and/or to reset the digital signal processor 141 and/or to disable the auditory stimulation in monaural as well as in binaural systems. The reset may be of any desired type causing a defined operation.

The above described systems allow changes of a plurality of individual operating programs. Thus, for example, it can be a good idea in many implant systems to replace the implant management system or parts thereof. This applies especially to the "housekeeping system" and analysis functions of the implant, such as for example:

charge control (for secondary power supply) and discharge monitoring (for secondary and primary power supply), energy optimization of the management system (for example, programmable or self-adapting cutoff of the hardware modules of the implant), optimized battery cell monitoring in systems with secondary power supply, especially as described advantageously in commonly assigned U.S. patent application Ser. No. 09/311,564, optimization of telemetry transmission software, replacement or reconfiguration of the remote control functions (also patient-specific) system messages within the implant to the patient, for example, on the charging state of a secondary power supply, for example as advantageously explained in commonly assigned U.S. patent application Ser. No. 09/311,566, telemetry transmission to the outside of sensor function(s) or sensor transmission functions, and audiometric implant functions.

In a completely implantable system which works only as a tinnitus masker or noiser or a system which executes both hearing aid and also tinnitus masker or noiser functions, the algorithms for signal generation for masking or the noiser function can advantageously be replaceable by software. This relates fundamentally to all aspects of signal generation, for example spectral location, level and phase ratios, etc. regardless of whether individual sine signals, narrowband signals or broadband signals are used.

In all these systems, the following advantages are achieved:

the hardware structure of the implant can be designed such that in case of program errors or external problems or storage damage or other fault-triggering events, the system is shifted into a nonharmful state safe to the patient (for example, by a watchdog unit, internally triggered "warm start" or externally triggered "cold start" (power on reset) of the implant system), transmission of the new operating software can take place with a fault-tolerant or fault-correcting code, transmission both of operating parameters as well as operating programs between the implantable system and the external unit can take place with inductive, infrared or electromagnetic processes, signal transmission can take place between the implantable system and the external unit using a "hand-shake protocol" and if there is a EEPROM storage area, the implant system can have a hardware module for programming of the EEPROM area.

What is claimed is:

1. An at least partially implantable system for rehabilitation of a hearing disorder, comprising:

an arrangement for at least one of processing and generating signals including an implantable hearing processor arrangement with control logic which operates according to an operating program and an implantable storage arrangement for storage of the operating program and of operating parameters;

a wireless telemetry means for data transmission between an implantable part of the system and an external unit; and a power supply arrangement which supplies individual components of the system with current;

wherein said implantable storage arrangement is rewritable and assigned to the processor arrangement for holding and reproducing the operating program and the operating parameters, of the processor arrangement and at least a portion of at least one of the operating program and of the operating parameters is adapted to be at least one of modified and replaced by data transmitted from the external unit via the telemetry means for changing the manner in which the processor arrangement will respond to at least one of a given audiological input and a power management input.

2. The system of claim 1, further including a buffer storage arrangement in which data transmitted from the external unit via the telemetry means is buffered before being relayed to the arrangement for at least one of processing and generating signals.

3. The system of claim 2, further including checking logic to check the data stored in the buffer storage arrangement before the data is relayed to the arrangement for at least one of processing and generating signals.

4. The system of claim 3, including a microcontroller for controlling the arrangement for at least one of processing and generating signals.

5. The system of claim 4, wherein the checking logic and the buffer storage arrangement are implemented in the microcontroller.

6. The system of claim 4, further including an implantable working storage arrangement for storage of a working program for the microcontroller, and wherein at least parts of the working program for the microcontroller can be at least one of changed and replaced by data transferred from the external unit via the telemetry means.

7. The system of claim 1, wherein said implantable storage arrangement includes at least two storage areas for holding and reproducing at least the operating program.

8. The system of claim 2, wherein the buffer storage arrangement includes at least two storage areas for holding and reproducing data transferred from the external unit via the telemetry means.

9. The system of claim 1, wherein a preprogrammed read only memory area which cannot be overwritten is assigned to the processor arrangement.

10. The system of claim 1, wherein the telemetry means has means for transferring operating parameters between the implantable part of the system and the external unit.

11. The system of claim 1, wherein said process arrangement includes a digital arrangement for generation of electrical signals and an arrangement downstream of the digital arrangement for generating stimuli based on the electrical signals generated by the digital arrangement.

12. The system of claim 1, wherein said process arrangement comprises a digital arrangement, at least one acoustic sensor, an arrangement for generating stimuli based on processing of the acoustic signals acquired by said at least one acoustic sensor, and a digital arrangement for processing the acoustic signals acquired by means of said at least one acoustic sensor.

13. The system of claim 12, wherein said arrangement for at least one of processing and generating signals includes a preprocessing arrangement for at least one of linear and nonlinear amplification and filtering of signals originating from said at least one acoustic sensor.

14. The system of claim 13, wherein the preprocessing arrangement comprises an anti-aliasing filter.

15. The system of claim 12, wherein said at least one acoustic sensor includes a plurality of acoustic sensors, and said arrangement for at least one of processing and generating signals includes an analog-digital converter connected downstream of each of the plurality of acoustic sensors.

16. The system of claim 11, wherein said arrangement for at least one of processing and generating signals includes at least one digital-analog converter connected upstream of the arrangement for generating stimuli.

17. The system of claim 16, wherein the arrangement for generating stimuli includes a plurality of stimuli producers to which its own digital-analog converter is connected upstream.

18. The system of claim 12, wherein said arrangement for at least one of processing and generating signals includes at least one driver arrangement connected upstream of the digital arrangement for processing of stimuli and is adapted to process the signals delivered by the arrangement for at least one of processing and generating signals according to a mode of stimulation.

19. The system of claim 12, wherein the arrangement for generating stimuli has means for producing electrical stimuli and further includes an array of stimulation electrodes for application of electrical cochlea or brain stem stimuli.

20. The system of claim 12, wherein the arrangement for generating stimuli comprises at least one electroacoustic transducer.

21. The system of claim 12, wherein the arrangement for generating stimuli comprises at least one electromechanical transducer.

22. The system of claim 21, wherein the arrangement for generating stimuli comprises at least one piezoelectric transducer.

23. The system of claim 12, wherein the arrangement for generating stimuli comprises at least one electromagnetic transducer.

24. The system of claim 1, wherein the power supply arrangement includes a rechargeable electrochemical cell.

25. The system of claim 1, wherein the system is a binaural system for rehabilitation of a hearing disorder of both ears and includes two system units, one for each of the ears.

26. The system of claim 25, wherein the two system units are essentially identical to one another.

27. The system of claim 25, wherein one system unit is a master unit and the other system unit is designed as the slave unit controlled by the master unit.

28. The system of claim 1, further including a transcutaneously operable reset switch.

* * * * *